(12) United States Patent
Young

(10) Patent No.: US 10,780,227 B2
(45) Date of Patent: Sep. 22, 2020

(54) PRE-FILLED SYRINGE OR AUTOINJECTOR

(75) Inventor: Matthew Young, Cambridge (GB)

(73) Assignee: OVAL MEDICAL TECHNOLOGIES LIMITED, Cambridge (GB)

( * ) Notice: Subject to any disclaimer, the term of this patent is extended or adjusted under 35 U.S.C. 154(b) by 131 days.

(21) Appl. No.: 13/380,644

(22) PCT Filed: Jun. 23, 2010

(86) PCT No.: PCT/GB2010/001243
§ 371 (c)(1),
(2), (4) Date: Feb. 2, 2012

(87) PCT Pub. No.: WO2010/149975
PCT Pub. Date: Dec. 29, 2010

(65) Prior Publication Data
US 2012/0130318 A1    May 24, 2012

(30) Foreign Application Priority Data
Jun. 24, 2009 (GB) .................................. 0910934.9

(51) Int. Cl.
*A61M 5/24* (2006.01)
*A61M 5/20* (2006.01)
(Continued)

(52) U.S. Cl.
CPC ........ *A61M 5/2429* (2013.01); *A61M 5/2033* (2013.01); *A61M 5/002* (2013.01);
(Continued)

(58) Field of Classification Search
CPC .... A61M 2005/206; A61M 2005/3121; A61M 5/002; A61M 5/2033; A61M 5/2429;
(Continued)

(56) References Cited

U.S. PATENT DOCUMENTS 2,193,489 A * 3/1940 Nevin ................. A61M 5/2448
206/438
3,075,528 A * 1/1963 Lundgren ................. A61J 1/06
604/403
(Continued)

FOREIGN PATENT DOCUMENTS

AU        198811602      8/1989
CN       1874810 A      12/2006
(Continued)

OTHER PUBLICATIONS

United Kingdom Intellectual Property Office Search Report for GB0910934.9, dated Oct. 2009.
(Continued)

*Primary Examiner* — Nathan R Price
*Assistant Examiner* — Weng Lee
(74) *Attorney, Agent, or Firm* — Lando & Anastasi, LLP

(57) ABSTRACT

The invention provides a syringe for dispensing a drug (1), comprising: a rigid syringe body, —a first container (2), in contact with and enclosing the drug; and a second container (3), enclosing the first container, the second container being less gas permeable than the first container, wherein the second container partially or fully forms the rigid syringe body or is held within the rigid syringe body. The invention preserves the drug but allows the drug to be easily accessed without the need for a user to remove a gas barrier structure as a separate action in addition to the other actions needed to deliver the drug.

15 Claims, 22 Drawing Sheets

(51) Int. Cl.
*A61M 5/28* (2006.01)
*A61M 5/00* (2006.01)
*A61M 5/31* (2006.01)

(52) U.S. Cl.
CPC ............. *A61M 5/286* (2013.01); *A61M 5/288* (2013.01); *A61M 2005/206* (2013.01); *A61M 2005/3121* (2013.01)

(58) Field of Classification Search
CPC .................. A61M 5/286; A61M 5/288; A61M 2005/3117; A61M 2005/312
See application file for complete search history.

(56) References Cited

U.S. PATENT DOCUMENTS

| | | | |
|---|---|---|---|
| 3,182,660 A * | 5/1965 | Weydanz | A61M 5/2033 604/139 |
| 3,507,386 A | 4/1970 | Ichiro | |
| 3,682,174 A | 11/1972 | Cohen | |
| 3,946,732 A | 3/1976 | Hurscham | |
| 4,214,584 A * | 7/1980 | Smirnov | A61M 5/19 604/135 |
| 4,227,528 A * | 10/1980 | Wardlaw | A61M 5/2033 604/139 |
| 4,378,015 A * | 3/1983 | Wardlaw | A61M 5/2033 604/137 |
| 4,424,057 A | 1/1984 | House | |
| 4,615,468 A | 10/1986 | Gay | |
| 5,092,843 A * | 3/1992 | Monroe | A61M 5/2066 604/137 |
| 5,244,465 A | 9/1993 | Michel | |
| 5,250,037 A | 10/1993 | Bitdinger | |
| 5,330,426 A * | 7/1994 | Kriesel | A61M 5/2429 604/82 |
| 5,354,286 A | 10/1994 | Mesa | |
| 5,360,410 A * | 11/1994 | Wacks | 604/232 |
| 5,527,580 A * | 6/1996 | Ikeda | B01L 3/50825 215/247 |
| 5,531,683 A * | 7/1996 | Kriesel et al. | 604/89 |
| 6,027,472 A | 2/2000 | Kriesel et al. | |
| 6,073,759 A | 6/2000 | Lambourne | |
| 6,331,174 B1 | 12/2001 | Reinhard | |
| 6,387,078 B1 * | 5/2002 | Gillespie, III | 604/181 |
| 7,708,719 B2 * | 5/2010 | Wilmot et al. | 604/236 |
| 2001/0004682 A1 | 6/2001 | Weston | |
| 2002/0007149 A1 | 1/2002 | Nelson | |
| 2003/0106824 A1 | 6/2003 | Wilmot | |
| 2003/0199814 A1 * | 10/2003 | Parsons | A61M 5/30 604/68 |
| 2008/0072992 A1 | 3/2008 | Baleriaux | |

FOREIGN PATENT DOCUMENTS

| | | |
|---|---|---|
| EP | 0458337 | 11/1991 |
| EP | 0473159 | 3/1992 |
| EP | 0665028 | 8/1995 |
| EP | 1679365 | 7/2006 |
| JP | 2001017546 A | 1/2001 |
| JP | 2001029466 A | 2/2001 |
| JP | 2003180827 A | 7/2003 |
| JP | 2004229750 A | 8/2004 |
| JP | 2004532756 A | 10/2004 |
| JP | 2007313335 A | 12/2007 |
| JP | 2008522659 A | 7/2008 |
| WO | WO-97/37628 | 10/1997 |
| WO | WO-00/71185 | 11/2000 |

OTHER PUBLICATIONS

International Search Report for PCT/GB2010/001243, dated Aug. 2010.
United Kingdom Intellectual Property Office Search Report for GB0912073.4, dated Oct. 2009.
International Search Report for PCT/GB2010/001244, dated Oct. 2010.
International Preliminary Report on Patentability for PCT/GB2010/001243, dated Jan. 2012.
International Preliminary Report on Patentability for PCT/GB2010/001244, dated Jan. 2012.
English Translation of First Office Action of the State Intellectual Property Office of the People's Republic of China from corresponding CN Application Serial No. 201080028000.2 dated Mar. 28, 2013.
English Translation of Notice of Reasons for Rejection from corresponding JP Application Serial No. 2012-516850 dated Jul. 15, 2014.
English Translation of Decision of Rejection from corresponding JP Application Serial No. 2012-516850 dated Jan. 6, 2015.
Examination Report of the Indian Patent Office from corresponding Indian Application Serial No. 429/DELNP/2012 dated Oct. 1, 2018.

* cited by examiner

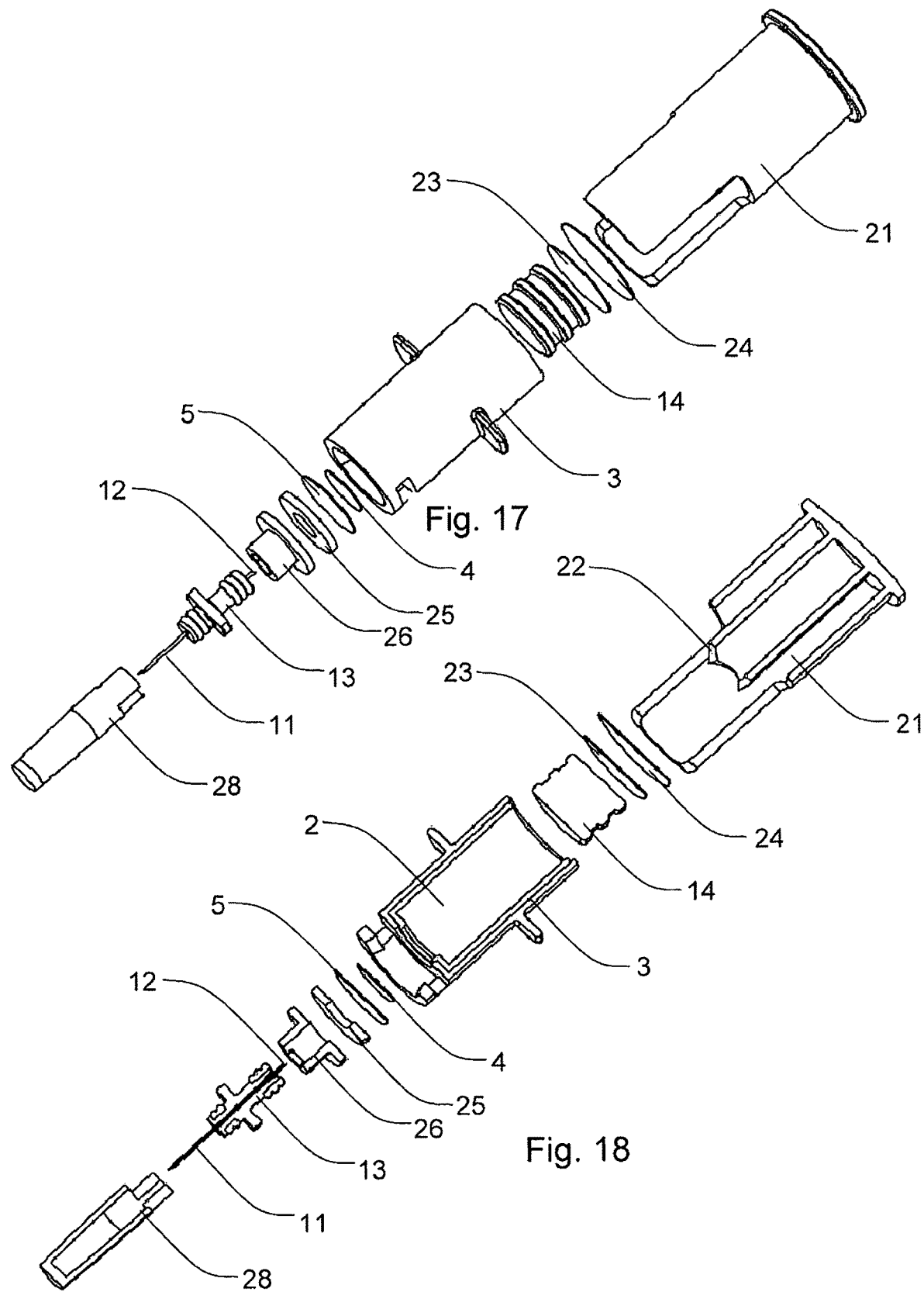

PRE-FILLED SYRINGE OR AUTOINJECTOR

CROSS REFERENCE TO RELATED APPLICATION

This application is a U.S. National Stage patent application of PCT/GB2010/001243, which designated the United States, filed Jun. 23, 2010, entitled A Pre-Filled Syringe or Autoinjector, which claims priority to Great Britain Patent Application No. 0910934.9, filed Jun. 24, 2009, the disclosures of which are expressly incorporated herein by reference.

FIELD OF THE INVENTION

This invention relates to devices for drug storage and drug administration to a patient.

BACKGROUND OF THE INVENTION

One type of drug delivery device known in the art is an injection apparatus which contains a medical, therapeutic, diagnostic, pharmaceutical or cosmetic compound (drug) before it is administered, and which is used to administer the compound through the skin of the patient via a hollow needle. Injection apparatus of this type include pre-filled syringes and auto-injectors.

A pre-filled syringe is a syringe which is filled with drug prior to distribution to the end user who will administer the drug to the patient. A pre-filled syringe typically includes a drug container in the form of a syringe body, an elastomeric plunger for expelling the drug, and either an attached hypodermic needle or else features to allow a needle to be attached by the user prior to administration of the drug so that the drug can be delivered directly from the syringe in which it is supplied through the needle into the patient. The user of the syringe will typically need to be trained in the skill of administering injections, and may be the patient themselves, a doctor, a nurse or other carer such as a family member.

Autoinjectors are used to reduce the skill needed to administer an injection compared with a pre-filled syringe. They are therefore more suitable than syringes for use by people who have not been trained in the skill of giving injections, and are often used to administer drugs for treating unplanned 'crisis' conditions such as anaphylactic shock or nerve gas poisoning where trained medical personnel may not be available. They are also used where it is advantageous for drugs to be administered in a home environment without the presence of trained medical personnel, for instance in the delivery of some drugs for treating cancer or auto-immune diseases. In this instance the person administering the drug may be the patient themselves or a family member who may have disabilities including limited strength, dexterity or vision.

Autoinjectors typically include a drug container in the form of a pre-filled syringe or cartridge along with a secondary structure which includes mechanisms to automatically insert a hypodermic needle into the patient and operate the plunger to administer the drug. The drug container is generally filled in an aseptic environment and then assembled to the secondary structure after it has left this aseptic environment. In this way the risk of particulate and biological contamination of the drug by exposure to the secondary structure is reduced. Examples of this type of device include the EpiPen from King Pharmaceuticals and the DAI from Scandinavian Health Limited.

In a similar way, pre-filled syringes may be assembled to additional structures outside the sterile filling environment after filling, such as needle safety mechanisms to prevent cross-contamination of blood borne diseases due to needle stick injuries after use.

These types of drug containers and syringes are typically made from glass because glass provides various benefits. Glass has good resistance to moisture and gas permeation. It has good transparency which allows the drug to be inspected after filling. It is also relatively inert to many drugs. However, glass has several disadvantages, including fragility and the ability to contaminate certain drugs.

An alternative group of materials, cyclic olefin polymers, has been used in the manufacture of syringes, as they have less of a contaminating effect on drugs and exhibit good transparency. These materials include cyclic olefin copolymers such as Topas from Topas Advanced Polymers GmbH, and cyclic olefin homopolymers such as Crystal Zenith from Daikyo. However these materials do not have the same resistance to gas permeability as glass so can allow greater permeation of atmospheric gases such as oxygen through the container into the drug, where the gases can cause the drug to degrade.

In order to resolve this issue of gas permeability, patent application US 2008/0072992 describes a drug container which may be made of cyclic olefin copolymer, and which is held within an envelope of a material which is less oxygen-permeable than the material of the container. However in order to access the drug, a user must first remove the envelope enclosing the drug container. This arrangement has the disadvantages that it increases the number of steps needed for a user to access the drug, and the envelope can obscure the drug during storage of the drug container making the drug more difficult or impossible to inspect prior to use. The envelope also increases the size of the overall drug packaging. There is also a risk that the user will remove the drug container prematurely from the envelope, causing the drug to be contaminated by oxygen. This is likely if the user is not aware of the function and importance of the envelope in protecting the drug from oxygen. Furthermore, users with physical disabilities may find it difficult to open the envelope.

SUMMARY OF THE INVENTION

The present invention is defined in the appended claims, to which reference should now be made.

The present invention aims to address some or all of the problems described above by providing a syringe or autoinjector which includes a drug contact container with internal drug-contact surfaces consisting primarily of a substantially non-contaminating material such as a cyclic olefin polymer, and a separate substantially gas-impermeable container to limit permeation of atmospheric gases such as oxygen into the drug, such that the drug can be easily accessed without the need for a user to remove the gas barrier structure as a separate action in addition to the other actions needed to deliver the drug.

In this way, a pre-filled syringe or autoinjector is provided that has a shelf-life comparable with glass, and which, from a user perspective, operates in the same way as glass pre-filled syringes, but without the disadvantages of glass. The gas-impermeable container encases the drug contact container so that damaging ingress of gas is substantially prevented. However, the gas impermeable container is part of the structure of the syringe and it is not necessary to completely remove it in order to dispense the drug.

It should be clear that the outer, less gas permeable, container must completely enclose the inner, more gas permeable container to be fully effective. So the term "enclosing" as used herein should be taken to mean "completely enclosing", so that oxygen or other contaminants from the outside environment cannot reach the drug without passing through some portion of the outer container. Both the first, inner container and the second, outer container, including any sealing elements forming part of those containers, completely envelop the drug.

The invention also aims to limit the number of potentially contaminating materials in contact with the drug during storage.

The invention also aims to provide a primary drug container which integrates with the secondary structure of the autoinjector or syringe in a way which brings benefits in terms of design, cost and robustness.

In one embodiment of the invention the syringe or autoinjector includes an inner container in contact with the drug which is made from a substantially gas-permeable rigid material such as a cyclic olefin polymer appropriate for contact with a drug. This inner container is contained within a separate secondary outer container which is made from a substantially gas-impermeable rigid material such as EVOH or polyamide. Substantially gas-impermeable as used herein means at least less gas permeable than the material of the drug contact container and sufficiently gas impermeable to allow the syringe or autoinjector to be stored for extended periods of time without degradation of the drug. The necessary degree of gas-impermeability will depend on the particular drug being stored and the required shelf-life of the syringe.

A plunger may be included within the inner container in order to expel the drug, and a plunger mechanism is included to move the plunger relative to the inner container in order to force the drug out of the container and into the patient, typically through a hollow hypodermic needle. The inner container has at least one opening which is closed by a first seal which comprises a material which is in contact with and which is compatible with the stored drug. The outer container has at least one opening which is closed by a second seal which is substantially impermeable to atmospheric gases such as oxygen. In this preferred embodiment, the operation of the plunger mechanism causes both the first seal and the second seal to be broken to allow the drug to be dispensed into the patient.

The containers or seals may be broken by being pierced, by manual removal of a sealing element, by operation of a mechanical valve or by any other suitable means.

The first seal may be made from a thin membrane of thickness less than 1 mm so that it can be pierced easily in order to allow the drug to be dispensed. It may also include a cyclic olefin polymer material in order to provide a material in contact with the drug which minimises contamination of the drug and which is similar or substantially identical to the material of the first container in contact with the drug, so that the number of different materials in contact with the drug during storage is minimised.

The second seal may be made from a thin membrane of thickness less than 1 mm so that it can be pierced easily in order to allow the drug to be dispensed. It may be made from a thin multi-layer laminate which includes a substantially gas-impermeable material such as aluminium, polyamide or a fluoropolymer. Other materials typically used in multi-layer laminate films for food packaging may also be used.

In another embodiment of the invention the inner container can be separated from the outer container, so that the inner container can be filled within a first appropriate environment, such as an aseptic environment, and then be subsequently assembled to the syringe body in a second environment in order to prevent the risk of particulate or biological contamination from the secondary container contaminating the drug. This second environment may or may not be aseptic, and may be isolated from the first environment by having a reduced atmospheric air pressure compared with the first environment or by being separated from it by one or more physical barriers, or both.

In one embodiment of the invention the outer substantially gas-impermeable container forms a part of a secondary structure of the autoinjector or syringe, and is pre-assembled to it before the inner substantially gas-permeable container is filled or assembled to the secondary structure.

In another embodiment the outer and inner containers, or at least portions thereof, are co-moulded together.

In another embodiment of the design the outer container comprises an inner component which includes a gas-impermeable material sensitive to moisture such as EVOH or Polyamide, and an outer component which includes a moisture barrier material such as PET or a cyclic olefin polymer. These two components may be produced separately and assembled together or co-moulded together as a single component.

In another embodiment the inner and outer containers (or portions thereof) are formed from a three-shot moulding, comprising an inner drug contact layer, a middle layer of substantially gas impermeable material and an outer layer of substantially moisture impermeable material, in order to protect the substantially gas impermeable material from excessive humidity.

In another embodiment of the design the inner substantially gas-permeable container and outer substantially gas-impermeable container (or portions thereof) are co-moulded together, and positioned within a third separate substantially moisture-impermeable container, to prevent the substantially gas-impermeable materials of the outer container from excess atmospheric humidity.

In another embodiment the first and second seals are formed together from a multi-laminate foil comprising a drug-sealing material in contact with the drug and a substantial gas-impermeable material on the opposite side of the drug sealing material to the drug.

In another embodiment the first or second seal or both seals of the syringe or autoinjector are broken due to removal of a sterile needle cover prior to operation of the plunger mechanism.

In another embodiment of the invention the outer container is formed by a coating applied to the outer surfaces of the inner container. Typically this coating comprises an oxide such as silicon oxide or aluminium oxide.

BRIEF DESCRIPTION OF THE DRAWINGS

Examples of the present invention will now be described in detail with reference to the accompanying drawings, in which:

FIG. 17 shows an exploded view of the syringe of FIG. 15;

FIG. 18 shows an exploded section view of the syringe of FIG. 15;

DETAILED DESCRIPTION

Figure 1:
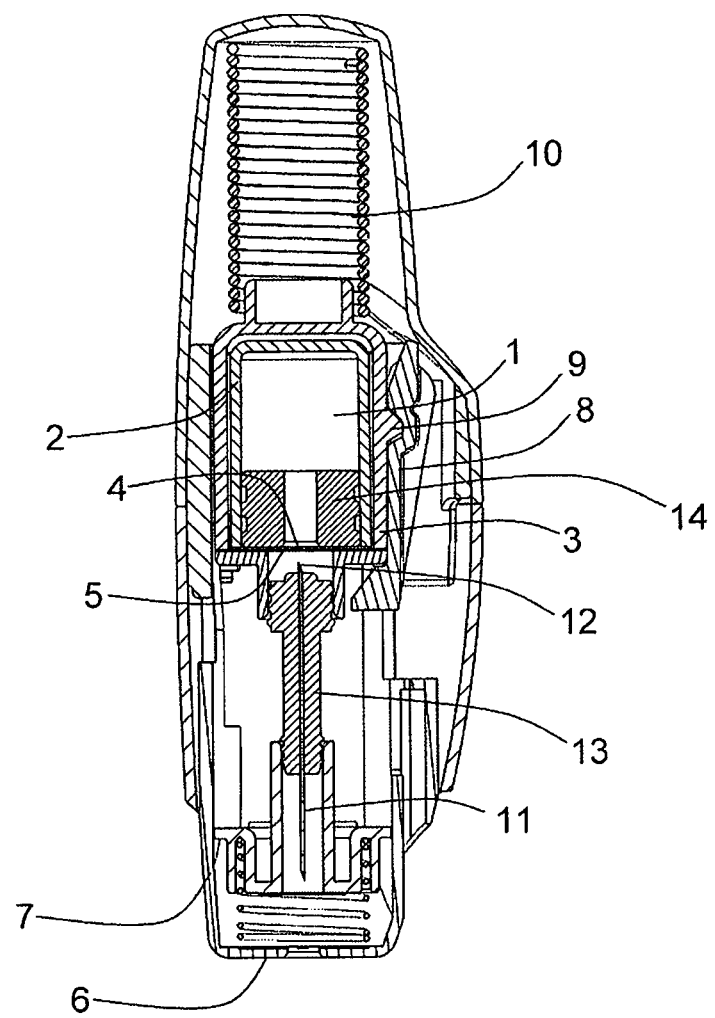
FIG. 1 is a longitudinal cross-section of an example of an autoinjector in accordance with the present invention.
Figure 2:
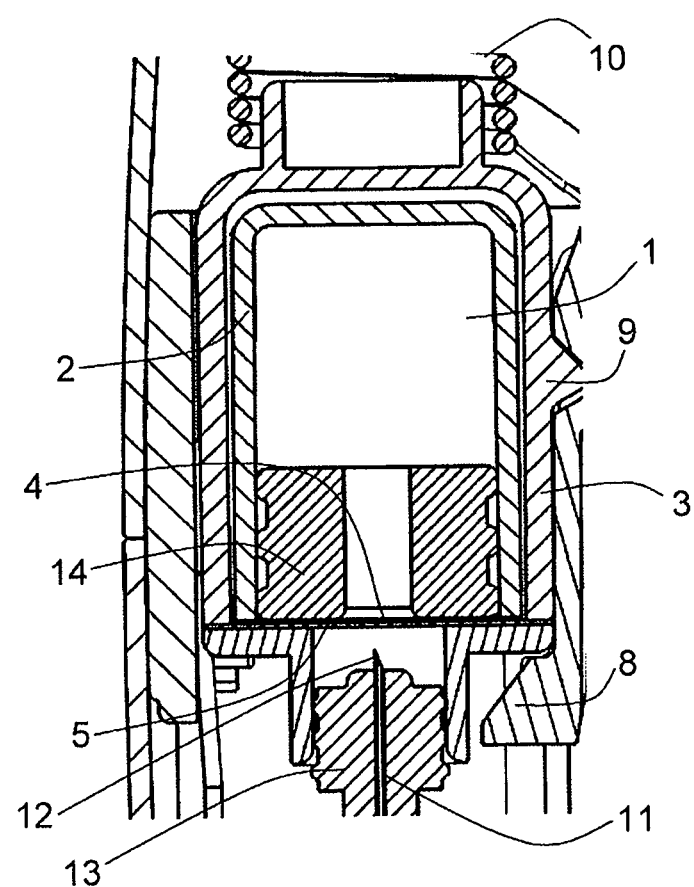
FIG. 2 is a part view of FIG. 1 shown at a larger scale for clarity.

FIG. 1 shows a section view of an example of an autoinjector in accordance with the present invention. The drug 1 is housed in a substantially gas-permeable inner container 2 which preferably includes a cyclic olefin polymer or other drug-compatible material in contact with the drug 1. This is enclosed within a substantially gas-impermeable outer container 3. The inner container 2 is sealed with a first substantially gas-permeable seal 4 which preferably includes a cyclic olefin polymer or other drug-compatible material in contact with the drug 1. The outer container 3 is sealed by a substantially gas-impermeable second seal 5. This is shown in FIG. 2, at larger scale for clarity.

The outer container is made from a substantially gas-impermeable rigid material such as EVOH or polyamide.

Both the inner and outer containers are held within a rigid syringe body which includes an outer housing, needle shield 7, locking arm 8 and needle-holding hub 13.

In order to activate the autoinjector, the front of the autoinjector 6 is pressed onto the patient's skin, which causes the needle shield 7 to move, releasing a locking arm 8 which is engaged with an engaging detail 9 on the external surface of the outer container 3. This allows the locking arm 8 to disengage with the engaging detail 9, releasing a main drive spring 10. This main drive spring 10 is arranged so that it can drive the inner container 2 and outer container 3 axially through the autoinjector causing a hollow hypodermic needle 11 to be driven forward into the patient. The spring 10 also causes the first seal 4 and second seal 5 to be pierced by a piercing detail 12 on the back of the hollow hypodermic needle 11. The needle 11 is attached to the needle-holding hub 13 which continues to move relative to the inner container 2 after the seals 4 and 5 have been pierced due to the force of the spring 10. This in turn causes the plunger 14 to be driven axially through the inner container 2 expelling the drug 1 through the needle 11 and into the patient.

Figure 3:
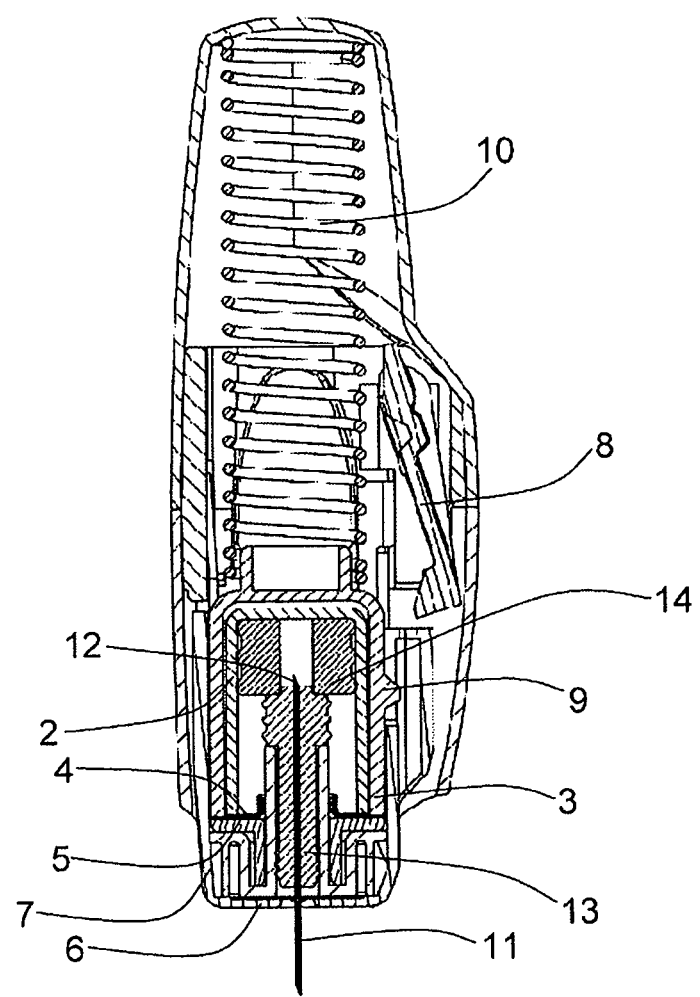
FIG. 3 is longitudinal cross-section of the autoinjector of FIG. 1 at a point after the drug has been administered to a patient.
Figure 4:
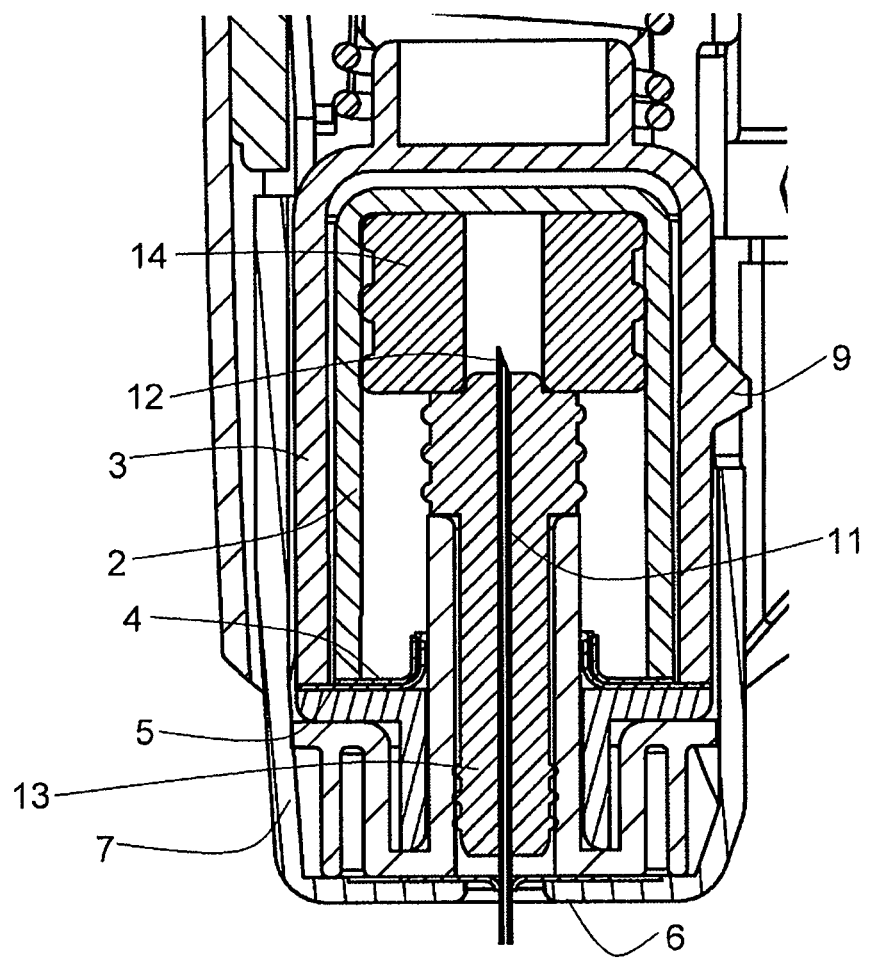
FIG. 4 is a part view of FIG. 3 shown at a larger scale for clarity.

FIG. 3 shows a section view of the autoinjector of FIG. 1 at a point after the drug has been administered to the patient. The plunger 14 has moved relative to the inner container 2 to expel the drug through the needle 11. The first seal 4 and second seal 5 have been broken by the needle 11 and the needle holding hub 13. FIG. 4 is a part view of FIG. 3 shown at a larger scale for clarity.

It will be obvious to those skilled in the art that this design can be implemented in different ways. For instance, the seals could be pierced by a component other than the back of the needle, for instance part of the back of the needle holding hub 13.

Figure 5:
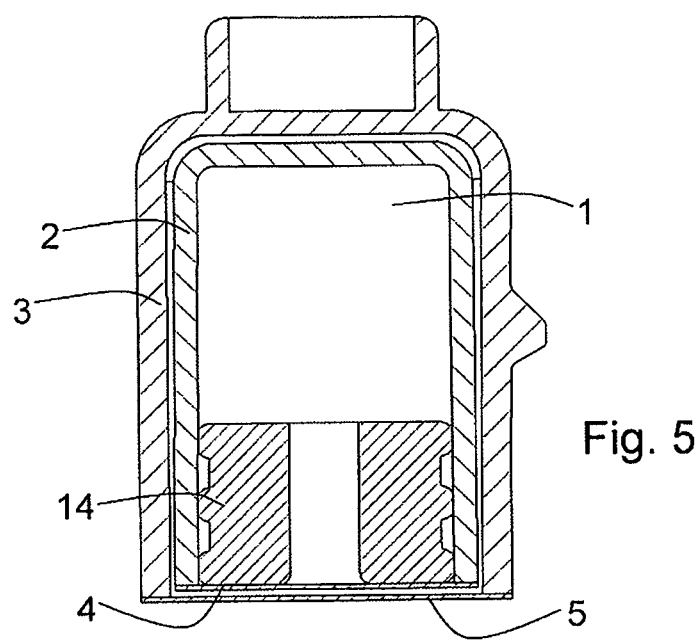
FIG. 5 shows a sectional view of a drug container and gas barrier arrangement in one embodiment of the invention.

FIG. 5 shows a sectional view of a drug container and gas barrier arrangement for one embodiment of the invention. This arrangement could be incorporated into a syringe or an autoinjector such as the autoinjector of FIG. 1, and comprises a drug 1, a separate, gas-permeable inner container 2 and substantially gas-permeable first seal 4, and a separate substantially gas-impermeable outer container 3 and second substantially gas-impermeable seal 5, and a plunger 14, as described above.

Figure 6:
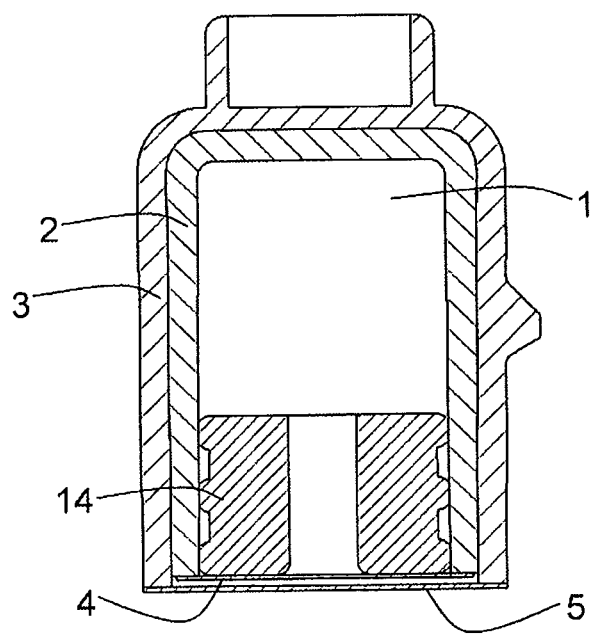
FIGS. 6-13 show sectional views of drug container and gas barrier arrangements for different embodiments of the invention.

FIG. 6 shows a sectional view of a drug container and gas barrier arrangement for another embodiment of the invention. This differs from the design of FIG. 5 in that it involves a substantially gas-permeable inner container 2 and a substantially gas-impermeable outer container 3 which are co-moulded together, with a separate substantially gas-permeable first seal 4 and separate second substantially gas-impermeable seal 5.

Figure 7:
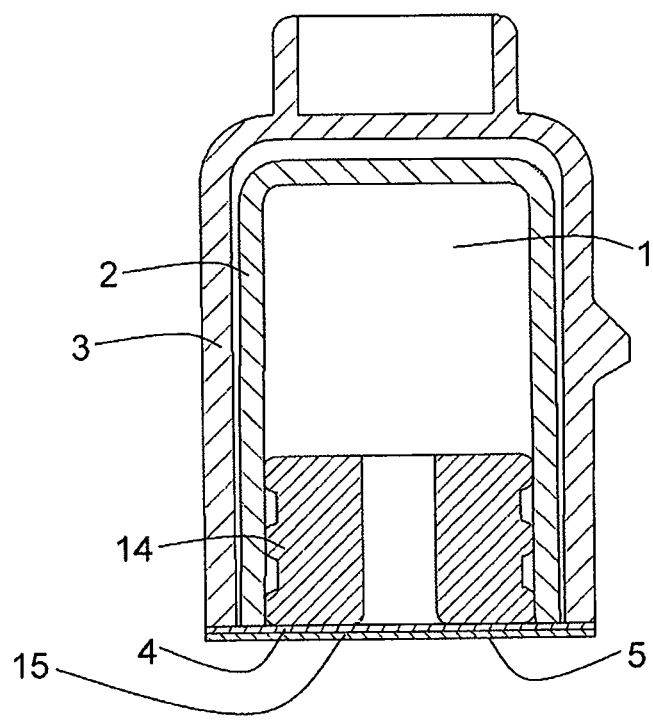

FIG. 7 shows a sectional view of a drug container and gas barrier arrangement for another embodiment of the invention. This differs from the design of FIG. 5 in that it involves a substantially gas-permeable inner container 2 and a separate substantially gas-impermeable outer container 3, with a substantially gas-permeable first seal 4 in contact with the drug and second substantially gas-impermeable seal 5 joined to the back of the first seal 4 on the opposite side from the drug 1 so that the two seals comprise a single multi-laminate film 15 which seals both the substantially gas-permeable inner container 2 and the substantially gas-impermeable outer container 3.

Figure 8:
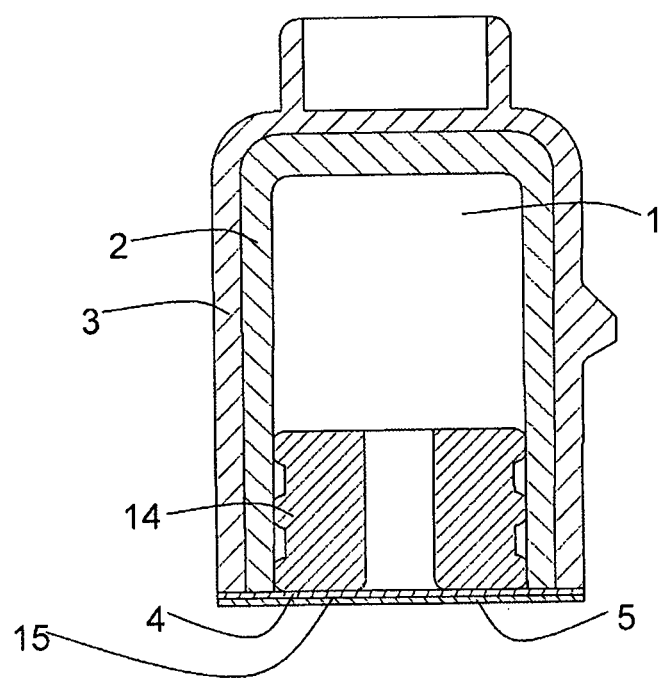

FIG. 8 shows a sectional view of an alternative version of the design shown in FIG. 6 incorporating a single multi-laminate film 15 which seals both the substantially gas-permeable inner container 2 and the substantially gas-impermeable outer container 3 as described above for FIG. 7.

Figure 9:
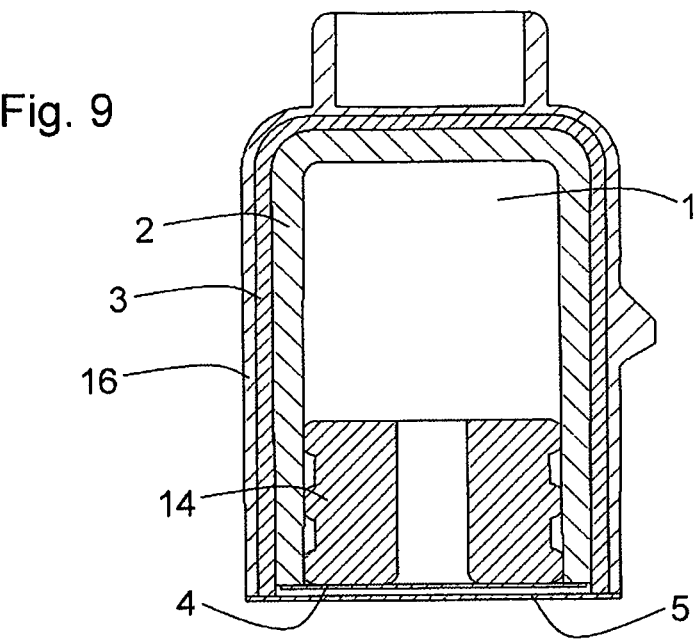

FIG. 9 shows a sectional view of an alternative version of the design shown in FIG. 6 which incorporates a third co-moulded layer of substantially moisture-impermeable material 16 which protects the substantially gas-impermeable outer container 3 from excessive humidity. Typically the inner container 2, the outer container 3 and the third layer 16 are all co-moulded together. The design incorporates a separate substantially gas-permeable first seal 4 and separate second substantially gas-impermeable seal 5.

Figure 10:
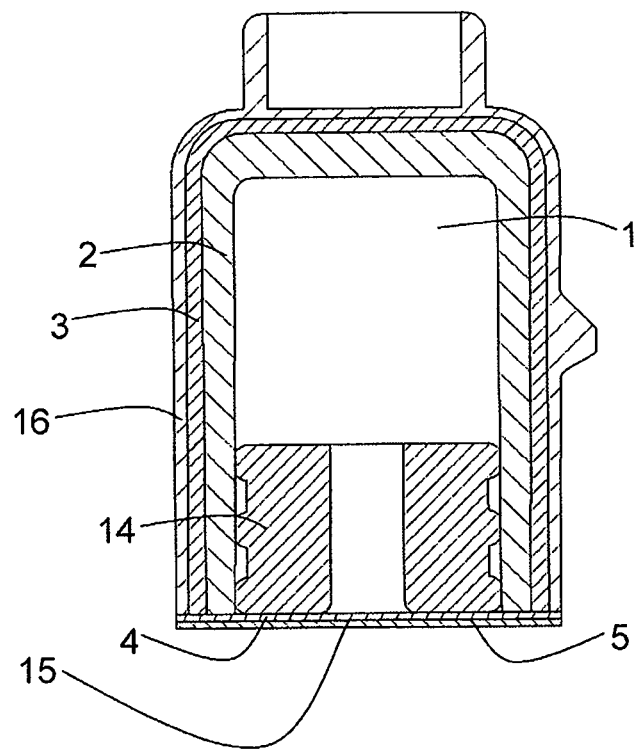

FIG. 10 shows a sectional view of an alternative version of the design shown in FIG. 9 which incorporates a single multi-laminate film 15 which seals both the substantially gas-permeable inner container 2 and the substantially gas-impermeable outer container 3 as described above for FIG. 7.

Figure 11:
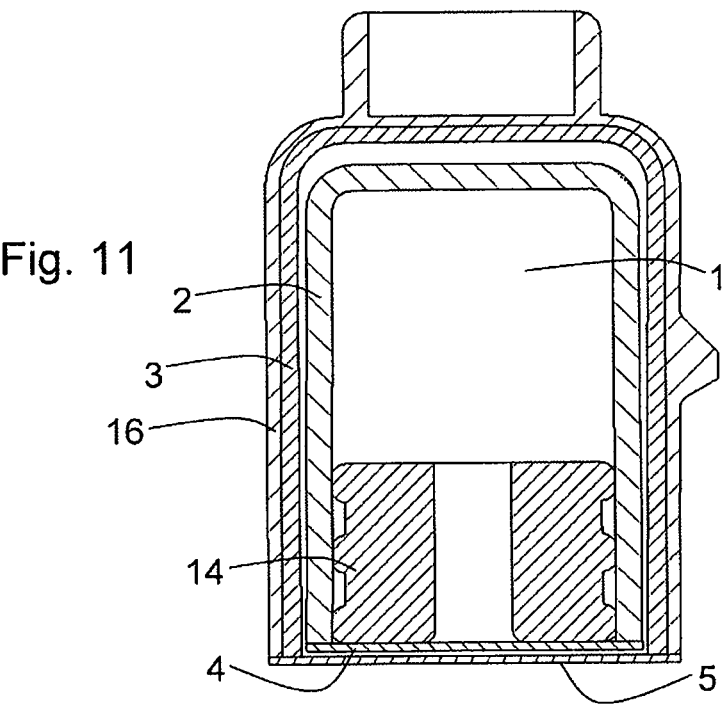

FIG. 11 shows an alternative version of the design shown in FIG. 5 where a separate substantially gas-impermeable outer container 3 incorporates an additional co-moulded layer of substantially moisture-impermeable material 16 which protects the substantially gas-impermeable outer container 3 from excessive humidity.

Figure 12:
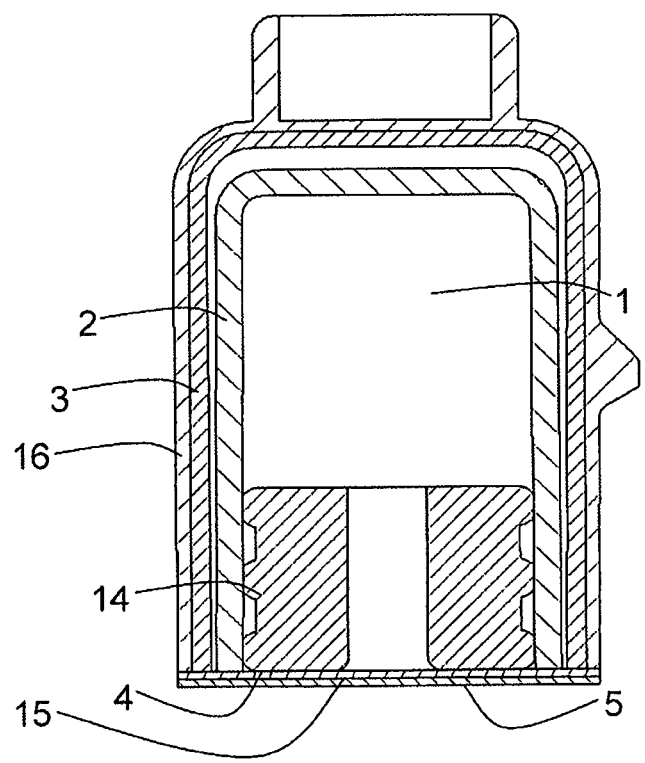

FIG. 12 shows an alternative version of the design shown in FIG. 11 which incorporates a single multi-laminate film 15 which seals both the substantially gas-permeable inner container 2 and the substantially gas-impermeable outer container 3 as described above for FIG. 7.

Figure 13:
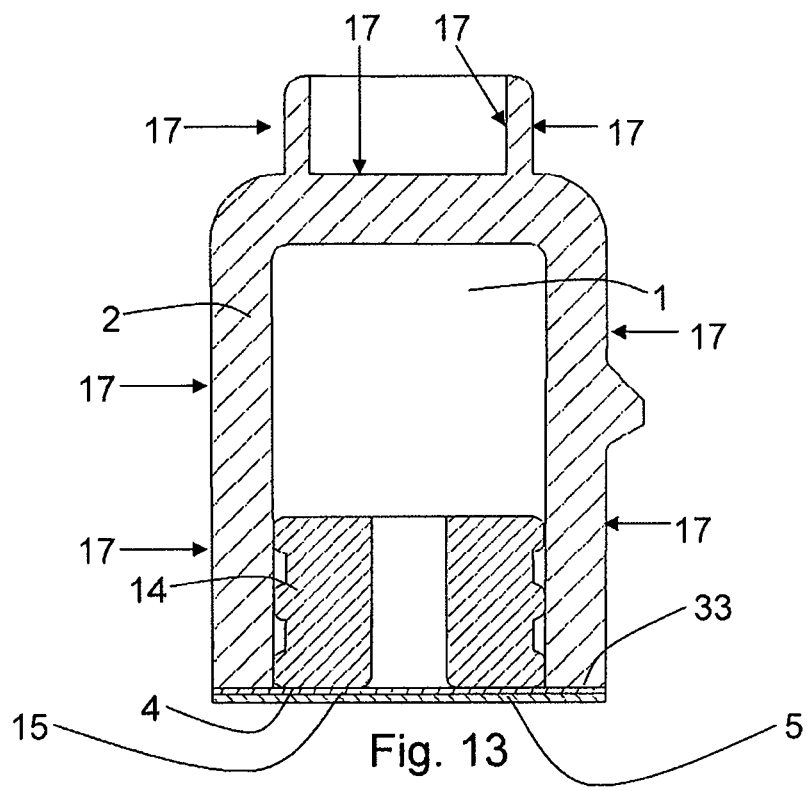

FIG. 13 shows an alternative version of the design shown in FIG. 7 where the outer container comprises a thin coating 17 of a substantially gas-impermeable material such as silicon oxide or aluminium oxide applied to the external surfaces of the substantially gas-permeable inner container 2. This coating may or may not extend partially or all of the way across that surface of the inner container 33 which is sealed to the combined first and second seals 15.

Figure 14:
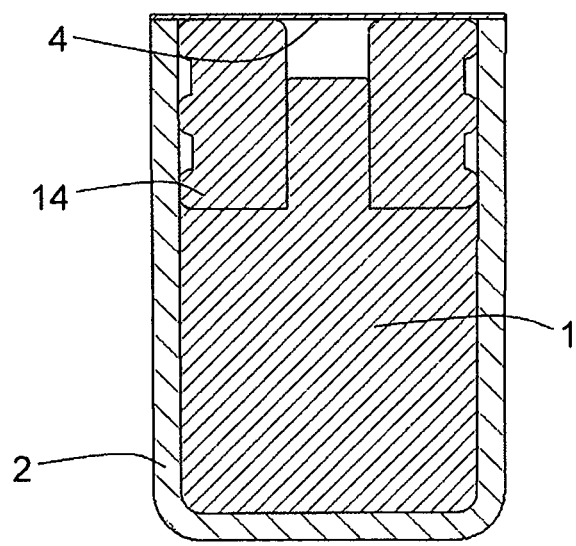
FIG. 14 shows a section view of an example of a substantially gas-permeable inner container containing a plunger and filled with drug and sealed with a substantially gas-permeable first seal in accordance with the invention.

FIG. 14 shows a section view of an example of a separate substantially gas-permeable inner container 2 containing a plunger 14 and filled with drug 1 and sealed with a substantially gas-permeable first seal 4.

In all of the designs of FIGS. 5 to 14, the inner container 2 is enclosed by the outer container 3, preventing any significant ingress of gases, and in particular oxygen, into the drug contact container. This is necessary in order to provide for a sufficient shelf-life for many drugs.

It is envisaged that any of the designs embodied in FIGS. 5 to 14 might constitute in whole or part that portion of an autoinjector or syringe which would be filled in a first appropriate environment such as an aseptic environment and then be subsequently assembled to part or all of the autoinjector or syringe in a second separate environment as described above.

Although not specifically illustrated here it is envisaged that any of the seals described above could be sealed to the appropriate container by any of a number of possible different means obvious to those skilled in the art. These means include heat welding, induction welding, laser welding, ultrasonic welding, spin welding, hot plate welding, use of an adhesive including ultraviolet light curing adhesive, and use of a separate retaining component with or without an additional elastomeric compression component where the separate retaining component is itself screwed, snapped or welded to the appropriate container.

Figure 15:
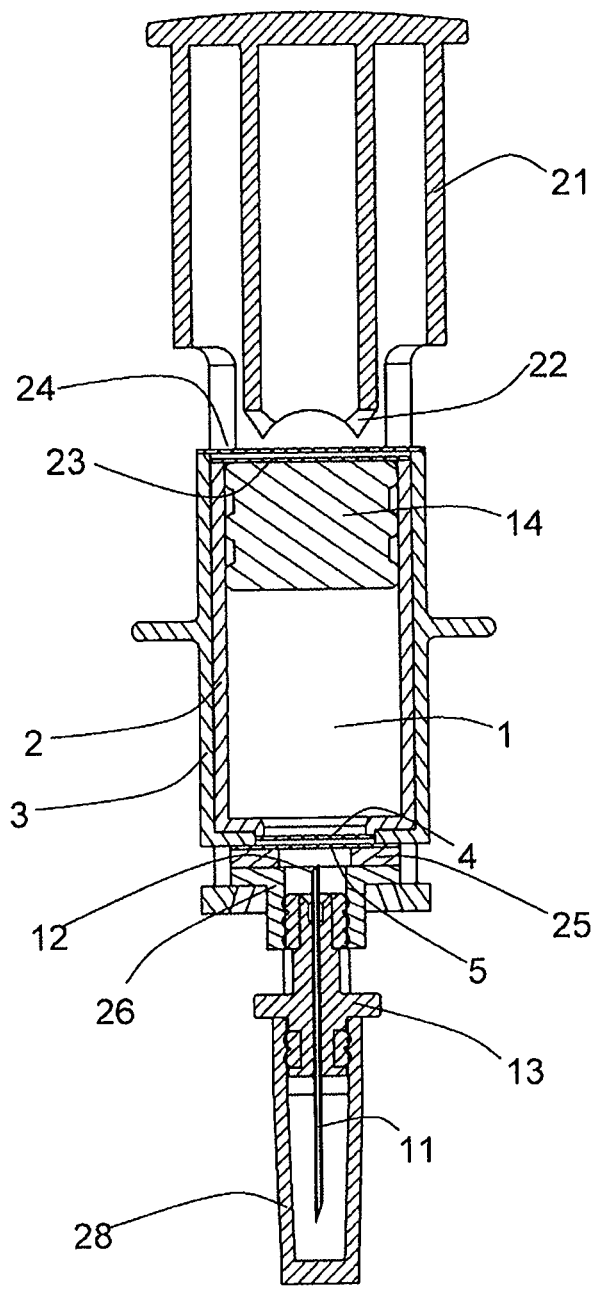
FIG. 15 shows a section view of an example of a syringe in accordance with the present invention.

FIGS. 15, 16, 17 and 18 illustrate another embodiment of the invention. FIG. 15 shows a section view of an example of a syringe in accordance with the present invention. The drug container and gas barrier arrangement is shown in detail in FIG. 19. The syringe incorporates a needle hub assembly which includes a needle cover 28 which can be removed by the user so that the needle hub assembly 13 can then be pushed back towards the substantially gas-permeable first seal 4 and substantially gas-impermeable seal 5 by the user so that a piercing detail 12 at the back of a needle 11 is caused to pierce both the aforementioned first substantially gas-permeable seal 4 and the aforementioned second substantially gas-impermeable seal 5 so that the drug 1 is placed in fluid communication with the hollow hypodermic needle 11. A dispensing button 21 can be pressed by the user to cause a piercing detail 22 to pierce another substantially gas-impermeable seal 24 forming part of the outer container and another substantially gas-permeable seal 23 forming part of the inner container and force the plunger 14 axially through the inner container 2 to expel the drug 1.

The needle cover 28 can be attached to the remainder of the syringe by a push fitting, as shown, by a screw fitting or by any other suitable means. Similarly, the needle-holding hub 13 can be coupled to the body of the syringe by a push fitting or a screw fitting.

Figure 16:
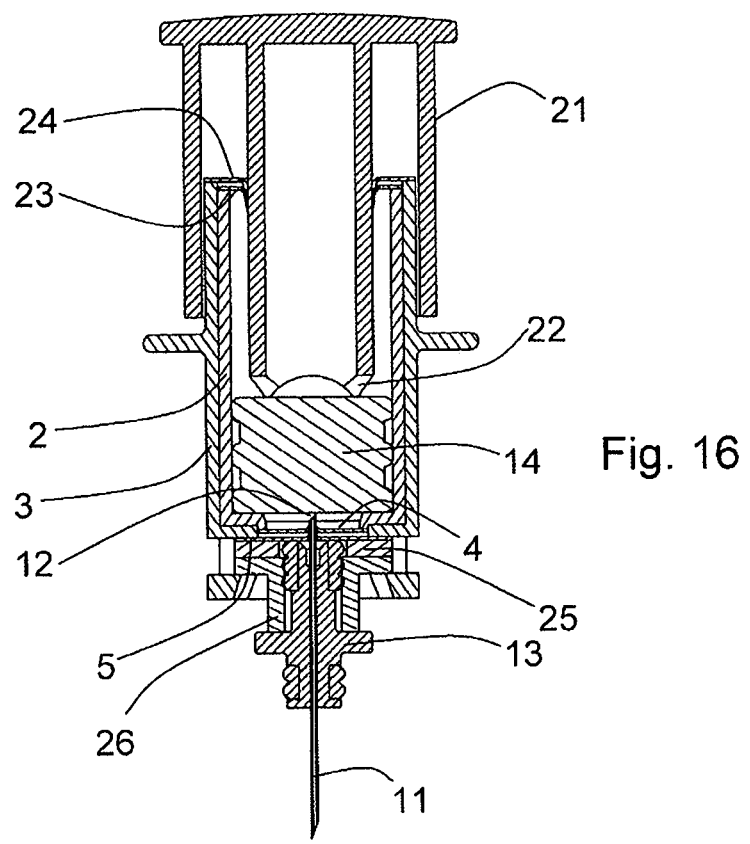
FIG. 16 shows a section view of the syringe of FIG. 15 at a point after the drug has been administered to a patient.

FIG. 16 shows the same syringe as shown in FIG. 15 at a point after the drug has been delivered.

FIG. 17 shows an exploded view of the syringe of FIG. 15.

FIG. 18 shows a sectional exploded view of the syringe of FIG. 15.

The needle-holding hub 13 is prevented from moving until desired by the user. This can be achieved in several ways, including mounting the needle cover 18 around the needle-holding hub so that it contacts the outer container of the syringe, or including a tear-off strip between the needle-holding hub and the body of the syringe.

It is also possible to incorporate a mechanism into the needle-holding hub such that removal of the needle cover 28 causes the needle-holding hub to move towards the drug container 2 and break the seals 4, 5. The needle-holding hub 13 can include a screw thread that is received in a threaded bore formed in the syringe body. The needle cap can also be connected to the needle-holding hub by a screw connection, such that initial rotation of the needle cover 28 causes rotation of both the needle cover and the needle holding hub, causing the needle-holding hub to travel along the threaded bore. This causes the needle to pierce the first and/or second seals. Continued rotation of the needle cover after the needle-holding hub has reached the end of the threaded bore, causes separation of the needle cover from the needle-holding hub.

Figure 19:
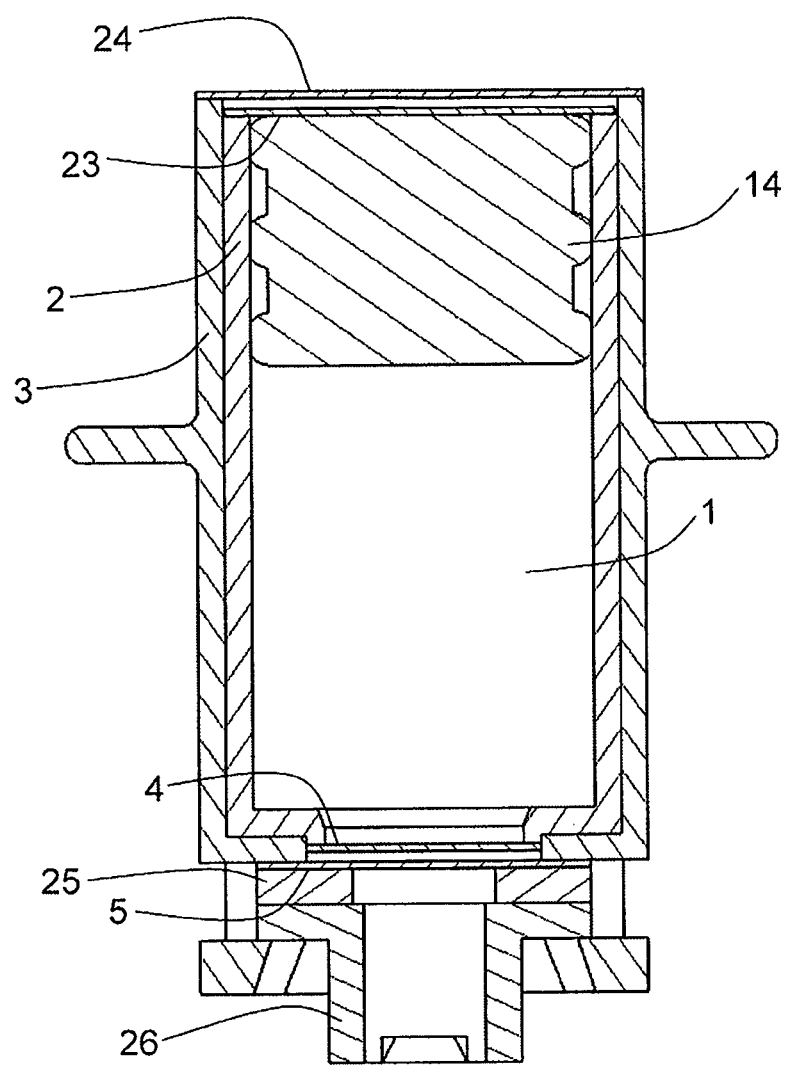
FIG. 19 shows a section view of the embodiment of the drug container and gas barrier arrangement of FIG. 15.

FIG. 19 shows a section view of the drug container and gas barrier arrangement of FIG. 15. This comprises a substantially gas-permeable inner container 2 and a substantially gas-impermeable outer container 3 co-moulded together. In this embodiment of the design a substantially gas-impermeable seal 5 is maintained in a sealing position against an opening in the substantially gas-impermeable outer container 3 due to the action of an elastomeric compression washer 25 retained by a compression washer retainer 26, and a separate substantially gas-permeable first seal 4 seals a substantially gas-permeable inner container 2.

The syringe of FIGS. 15-19 includes a rigid syringe body, held by the user when dispensing the drug. The rigid syringe body is formed by the dispensing button 21, the inner and outer containers 2, 3, retainer 26, needle hub assembly 13 and cover 28.

The other arrangements of seals and containers described in FIGS. 5-13 could equally be applied to the syringe design of FIGS. 15-18 and to other embodiments of syringes and autoinjectors.

Figure 20:
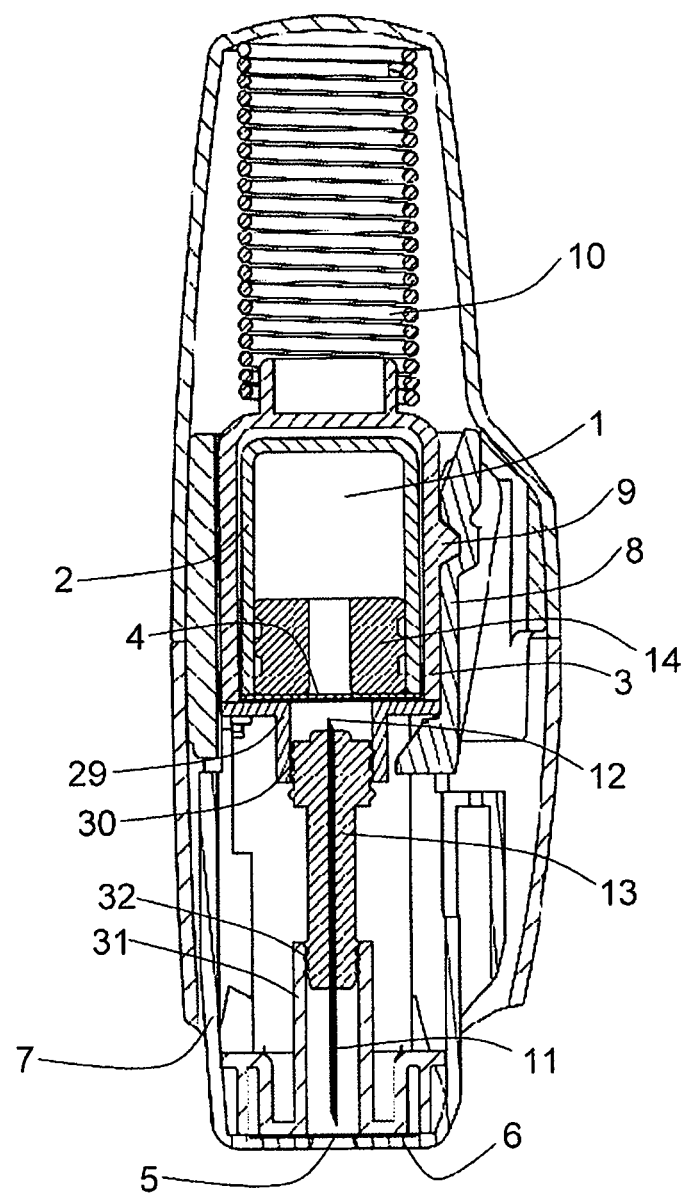
FIG. 20 shows a section view of an alternative embodiment of the invention incorporated into an autoinjector similar to that shown in FIGS. 1-4, but incorporating an alternative seal arrangement.

FIG. 20 shows a section view of an alternative version of the autoinjector of FIG. 1 where the substantially gas-impermeable seal 5 is positioned between the needle 11 and the front of the autoinjector 6 which is pressed against the patient during administration of the drug. The gas-impermeable seal 5 seals an opening in a substantially gas-impermeable lower sleeve 31 which contains a portion of the needle 11. A substantially gas-impermeable barrier is formed from the substantially gas-impermeable outer container 3, the substantially gas-impermeable lower container 29, a substantially gas-impermeable lower sleeve 31 and a substantially gas-impermeable needle-holding hub 13 which includes a substantially gas-impermeable sealing feature 30 which seals with the lower container 29 and a second substantially gas-impermeable sealing feature 32 which seals with the lower sleeve 31.

Figure 21:
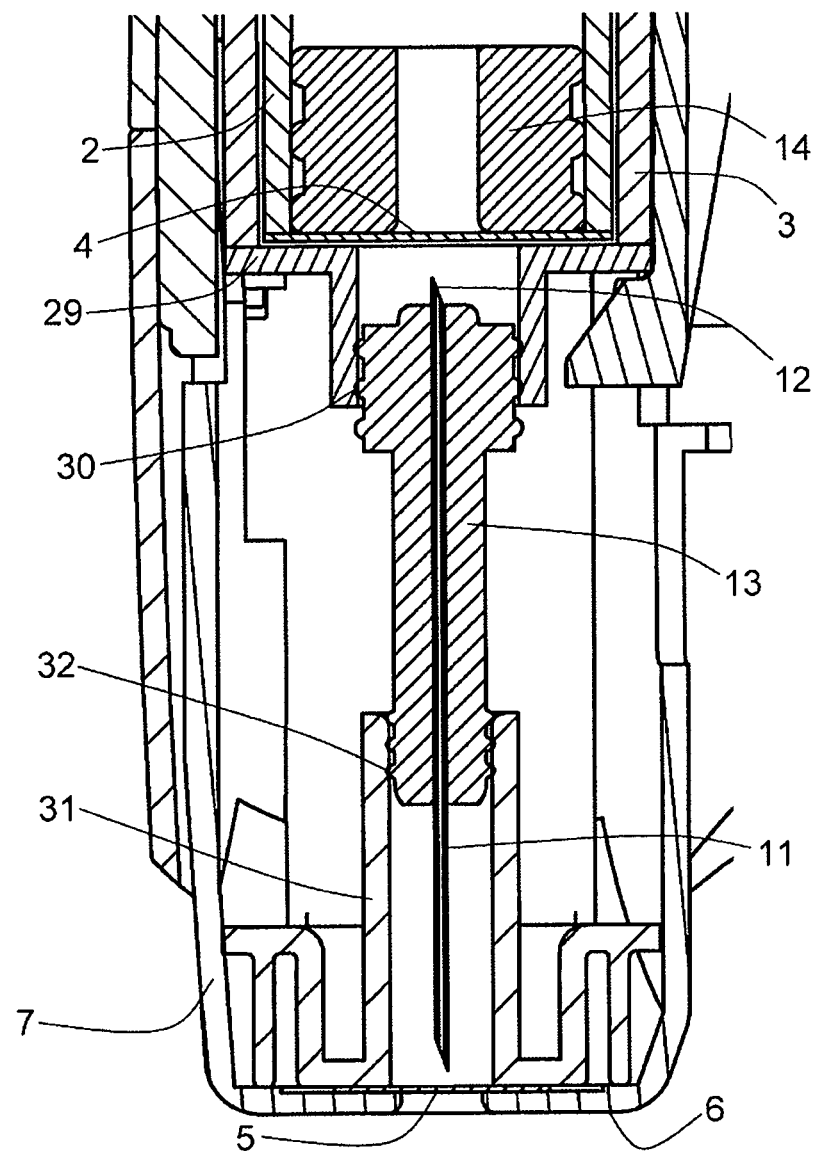
FIG. 21 is a part view of FIG. 20 shown at a larger scale for clarity.

FIG. 21 is a part view of FIG. 20 shown at a larger scale for clarity.

Figure 22:
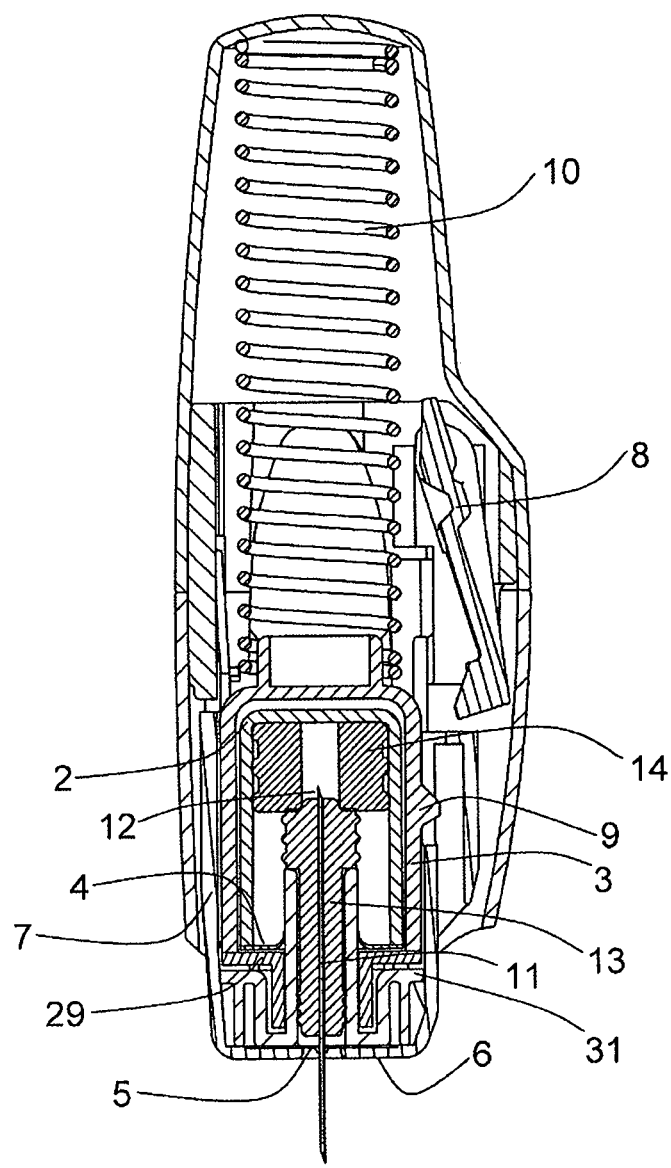
FIG. 22 is longitudinal cross-section of the autoinjector of FIG. 20 at a point after the drug has been administered to a patient.

FIG. 22 shows a section view of the autoinjector of FIG. 20 at a point after the drug has been administered to the patient. The plunger 14 has moved relative to the inner container 2 to expel the drug through the needle 11. The first seal 4 has been broken by the needle 11 and the needle holding hub 13 and second seal 5 has been broken by the other end of needle 11 nearest to the patient.

Figure 23:
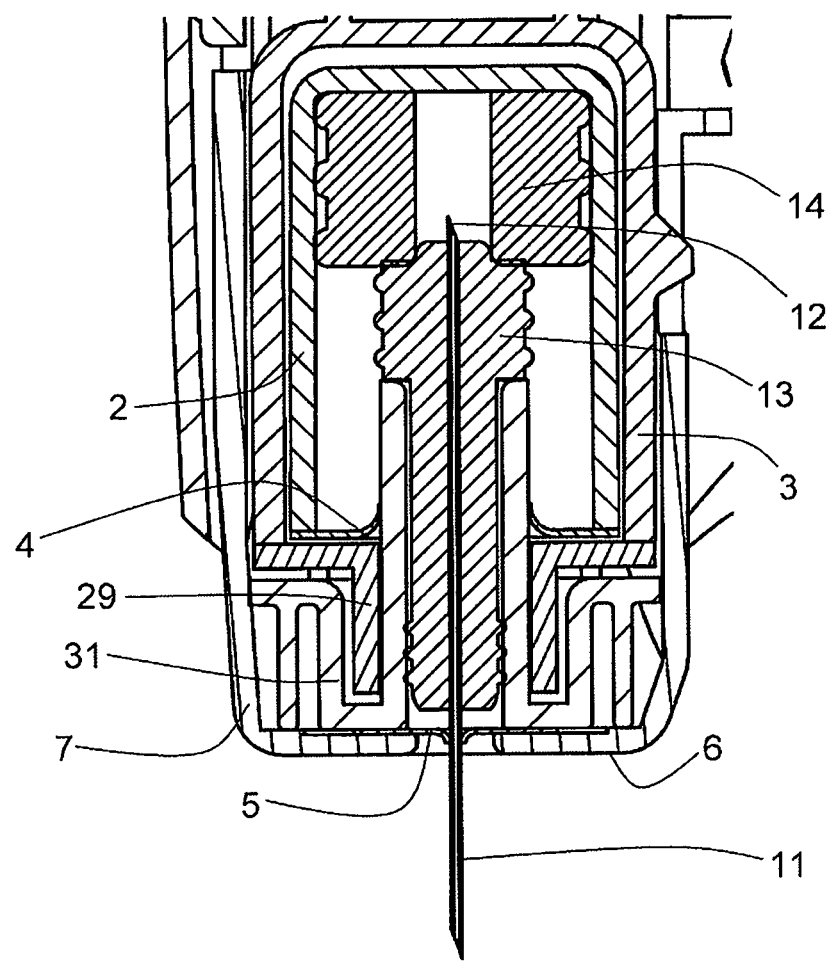
FIG. 23 is a part view of FIG. 22 shown at a larger scale for clarity.

FIG. 23 is a part view of FIG. 22 shown at a larger scale for clarity.

Figure 24:
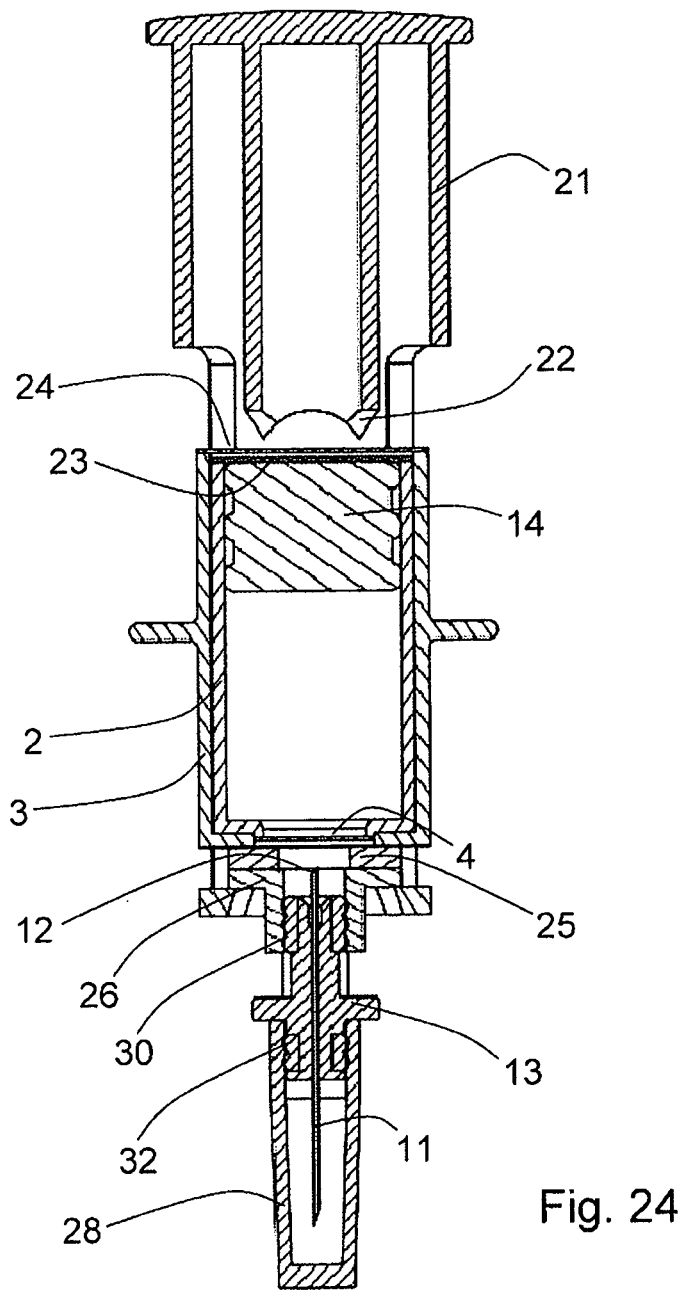
FIG. 24 shows a section view of an alternative embodiment of the invention incorporated into a syringe similar to that shown in FIGS. 15-18, but incorporating an alternative seal arrangement whereby the gas barrier is broached by removal of a needle shield.

FIG. 24 shows a section view of an alternative version of the syringe of FIG. 15 where a substantially gas-impermeable needle cover 28 which is removed by a user before administration of the drug to a patient comprises a substantially gas-impermeable seal. A substantially gas-impermeable container, which also forms the outer rigid body of the syringe, encloses the drug contact container 2, and is formed from the substantially gas-impermeable outer container 3, a substantially gas-impermeable upper seal 24, a substantially gas-impermeable elastomeric compression washer 25, a substantially gas-impermeable compression washer retainer 26, a substantially gas-impermeable needle-holding hub 13, which includes a substantially gas-impermeable sealing feature 30 which seals with the compression washer retainer 26 and a second substantially gas-impermeable sealing feature 32 which seals with the needle cover 28.

On removal of the needle cover 28, the user simply pushes the needle-holding hub 13 towards the drug container 2, in order that the needle 11 pierces the seal 4, allowing the drug to be dispensed through the needle.

Figure 25:
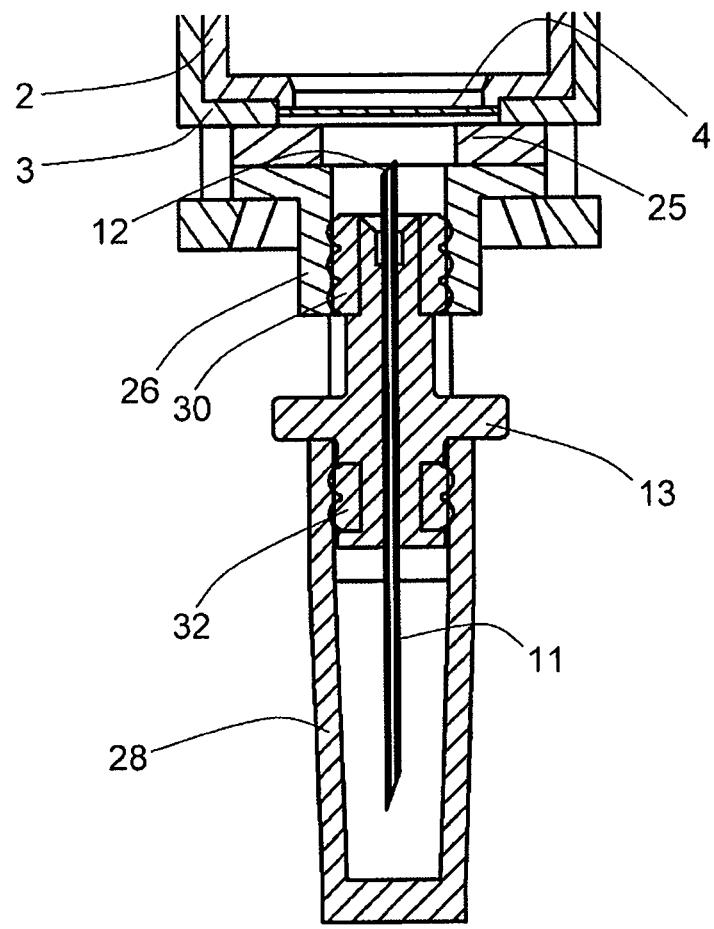
FIG. 25 is a part view of FIG. 24 shown at a larger scale for clarity.

FIG. 25 is a part view of FIG. 24 shown at a larger scale for clarity.

Figure 26:
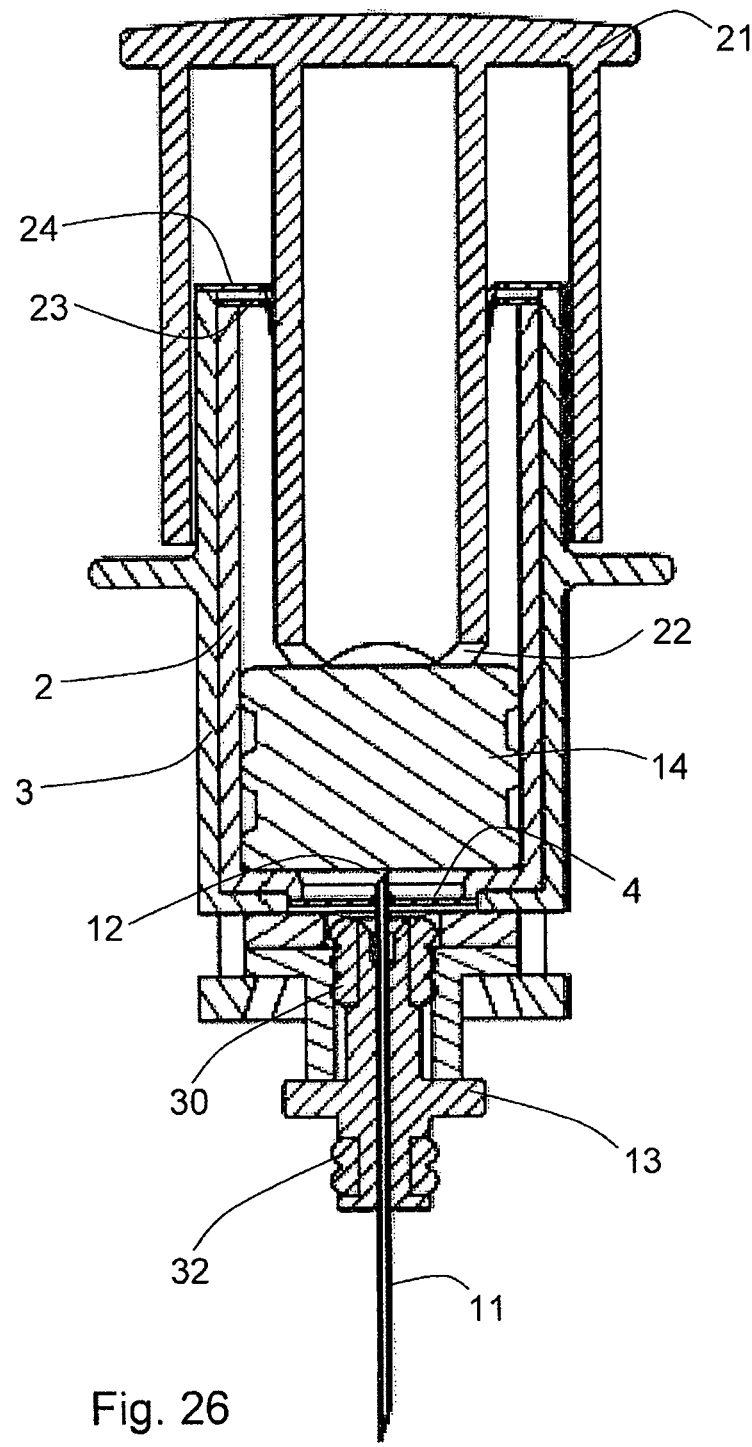
FIG. 26 is longitudinal cross-section of the autoinjector of FIG. 24 at a point after the drug has been administered to a patient.

FIG. 26 shows the same syringe as shown in FIG. 24 at a point after the needle cover 28 has been removed by a user and the drug has been delivered.

Figure 27:
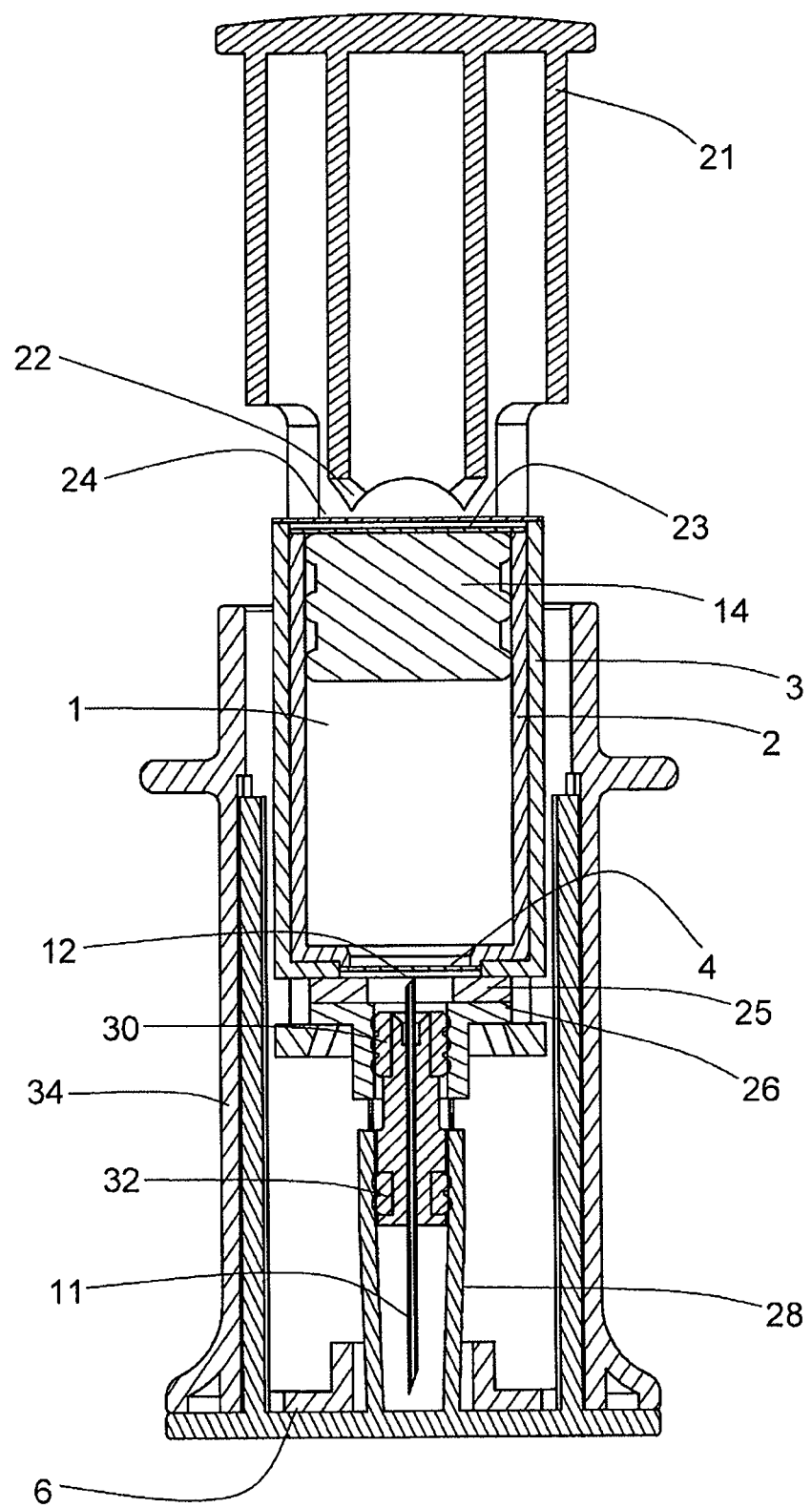
FIG. 27 shows a section view of an alternative embodiment of the syringe of FIG. 15 where the action of the user depressing a dispensing button causes a seal to be broken.

FIG. 27 shows an alternative version of the syringe of FIG. 24 where the action of the user pushing the button 21 causes the back of the needle 12 to pierce the substantially gas permeable seal 4. In order to administer the drug to the patient the user removes a manually removable needle shield 28, which forms part of the gas barrier as described for FIG. 24, and then applies the front of the syringe 6 to an appropriate area of the patient. The user then presses the button 21 which causes the inner substantially gas permeable container 2 and outer substantially gas impermeable container 3 to move axially towards the patient within rigid outer casing 34, causing the front of the needle 11 to move forwards into the patient and the rear of the needle 12 to pierce a substantially gas permeable seal 4. This movement of the button 21 also causes piercing details 22 to pierce an upper substantially gas impermeable seal 24 and an upper substantially gas permeable seal 23 and then cause the plunger 14 to be urged axially through the inner container 2 causing the drug to be urged through the needle 11 into the patient.

Figure 28:
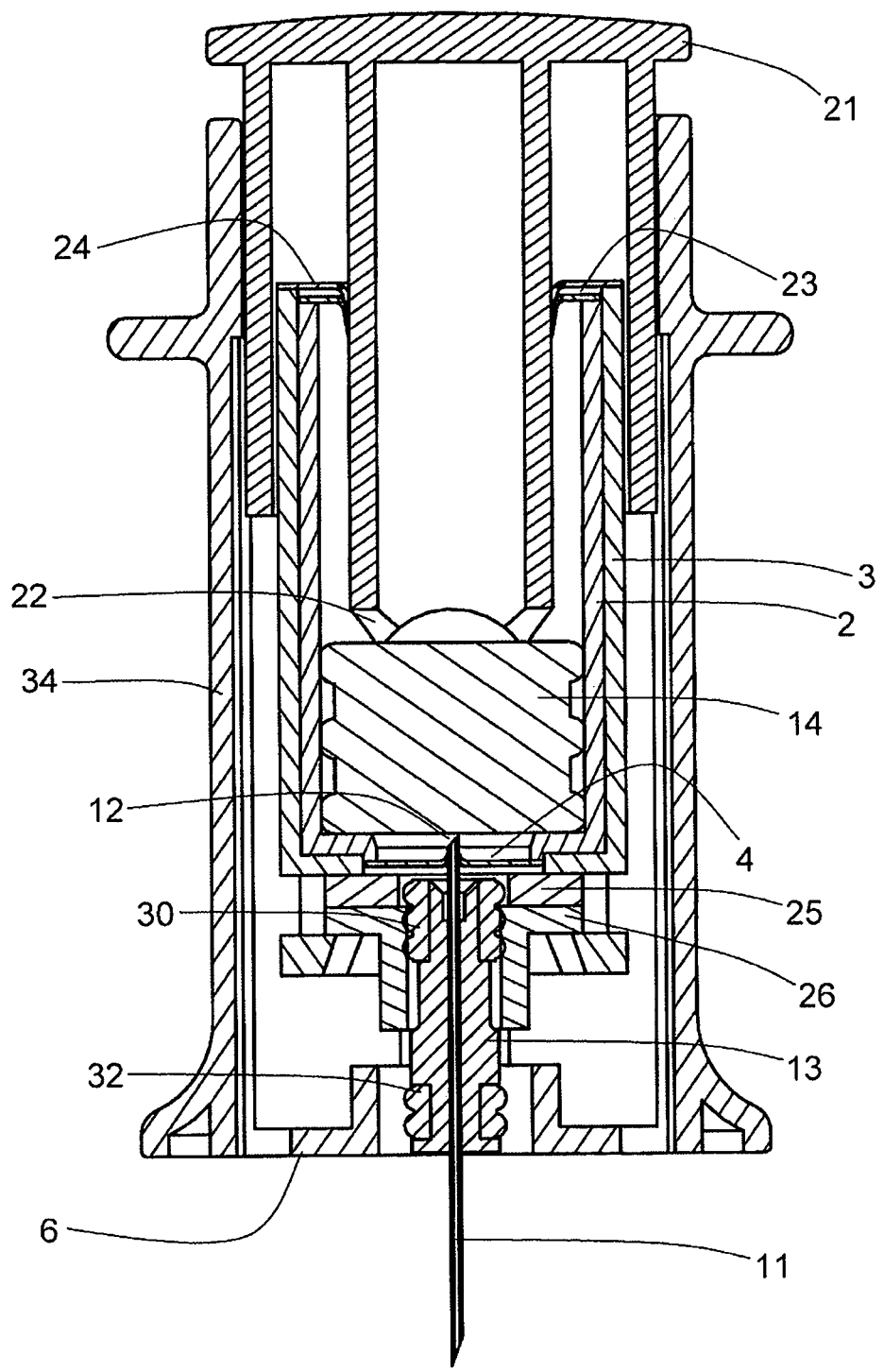
FIG. 28 shows a section view of the syringe of FIG. 27 at a point after the drug has been administered to a patient.

FIG. 28 shows the syringe of FIG. 27 at a point after the drug has been administered to the patient.

It will be obvious to those skilled in the art that the designs described above in FIG. 27 and FIG. 28 can be implemented in different ways. For instance, the seal 4 could be pierced by a component other than the needle such as the needle holding hub 13. The outer substantially gas-impermeable container could be sealed by a substantially gas impermeable seal 5 attached directly to it as described in FIG. 5 to FIG. 13 so that the seal 5 is pierced by the back of the needle 12 due to movement of the button 21. Features of FIGS. 27 and 28 could also be implemented in an autoinjector.

The invention claimed is:

1. A syringe for dispensing a drug, comprising:
   a rigid syringe body;
   a first container, in contact with and completely enclosing the drug;
   a second container, completely enclosing the first container so that any contaminants external to the second container must pass through a wall of the second container to reach the drug, the second container being less gas permeable than the first container, wherein the second container partially or fully forms the rigid syringe body or is held within the rigid syringe body; and
   a needle through which, in use, the drug is dispensed from the syringe, wherein the needle has a first end and a second end, and movement of a portion of the rigid syringe body relative to the first container causes the first end of the needle to breach the first container and the second container.

2. The syringe according to claim 1, wherein the syringe is an auto-injector.

3. The syringe according to claim 1, wherein the first container includes a first seal and wherein movement of the portion of the rigid syringe body causes the needle to breach the first seal.

4. The syringe according to claim 1, wherein the second container includes a second container seal and wherein movement of the portion of the rigid syringe body causes the needle to breach the second container seal.

5. The syringe according to claim 4, wherein the second container seal comprises a substantially oxygen impermeable material.

6. The syringe according to claim 1, wherein the first container is separate from the second container.

7. The syringe according to claim 1, wherein the first container and the second container are at least partially co-moulded.

8. The syringe according to claim 5, wherein the first container includes a first seal and the first seal is laminated with the second container seal.

9. The syringe according to claim 1, further comprising a plunger receivable in the first or second container for dispensing the drug from the first container.

10. The syringe according to claim 9, wherein the syringe includes a button configured to breach the first container and push the plunger within the first container to dispense the drug.

11. The syringe according to claim 10, wherein the button includes the portion of the rigid syringe body.

12. The syringe according to claim 1, the first container comprising cyclic olefin polymer material.

13. The syringe according to claim 1, the second container comprising one of EVOH and polyamide.

14. The syringe according to claim 1, wherein the first container includes a first seal and the second container includes a second seal and wherein movement of the portion of the rigid syringe body causes the needle to breach the first seal and the second seal.

15. The syringe according to claim 14, wherein the first container is separate from the second container.

* * * * *